US00PP36175P2

(12) United States Plant Patent
Blazejewski

(10) Patent No.: US PP36,175 P2
(45) Date of Patent: Oct. 1, 2024

(54) ***MANDEVILLA* PLANT NAMED 'BAHWHITE'**

(50) Latin Name: *Mandevilla sanderi*
Varietal Denomination: Bahwhite

(71) Applicant: VIVERO las FRESAS S.L., Vicar (ES)

(72) Inventor: Nicolas Blazejewski, Roquetas de Mar (ES)

(73) Assignee: VIVERO LAS FRESAS S.L., Vicar (ES)

( * ) Notice: Subject to any disclaimer, the term of this patent is extended or adjusted under 35 U.S.C. 154(b) by 0 days.

(21) Appl. No.: 18/512,800

(22) Filed: Nov. 17, 2023

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC ... A01H 5/02; A01H 5/00; A01H 6/08; A01H 6/088
See application file for complete search history.

(56) References Cited

U.S. PATENT DOCUMENTS

PP32,504 P2 * 11/2020 Graff ..... A01H 6/088 Plt./232

* cited by examiner

*Primary Examiner* — June Hwu
(74) *Attorney, Agent, or Firm* — C. Anne Whealy

(57) ABSTRACT

A new and distinct cultivar of *Mandevilla* plant named 'Bahwhite', characterized by its compact and broadly upright plant habit; moderately vigorous growth habit and moderate growth rate; freely branching habit; dark green-colored leaves; freely flowering habit; and white-colored flowers with bright yellow-colored throats.

2 Drawing Sheets

Figure 1:
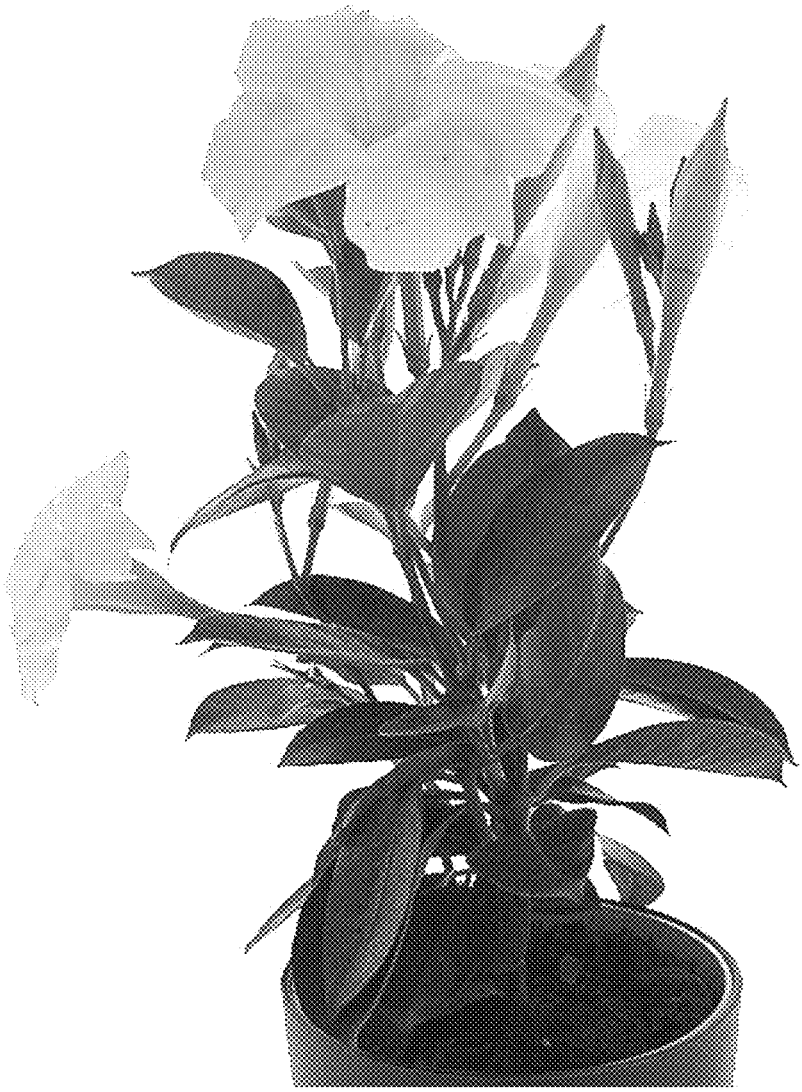

Botanical designation: *Mandevilla sanderi.*
Cultivar denomination: 'BAHWHITE'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Vivero las Fresas S.L. of Vicar, Spain on Feb. 3, 2023, application number 2023/0319. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'Bahwhite'.

The new *Mandevilla* plant is a product of a planned breeding program conducted by the Inventor in Vicar, Spain. The objective of the breeding program is to create new compact and freely branching *Mandevilla* plants with numerous attractive flowers.

The new *Mandevilla* plant originated from a cross-pollination conducted by the Inventor in Vicar, Spain in June, 2017 of a proprietary breeding selection of *Mandevilla sanderi* identified as code number 411, not patented, as the female, or seed parent with *Mandevilla sanderi* 'INMAN-WHIMP', disclosed in U.S. Plant Pat. No. 28,276, as the male, or pollen, parent. The new *Mandevilla* plant was discovered and selected by the Inventor as a single flowering plant from within the progeny of the stated cross-pollination in a controlled greenhouse environment in Vicar, Spain in April, 2020.

Asexual reproduction of the new *Mandevilla* plant by vegetative cuttings in a controlled greenhouse environment in Vicar, Spain since June, 2020 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bahwhite'. These characteristics in combination distinguish 'Bahwhite' as a new and distinct *Mandevilla* plant:

1. Compact and broadly upright plant habit.
2. Moderately vigorous growth habit and moderate growth rate.
3. Freely branching habit.
4. Dark green-colored leaves.

5. Freely flowering habit.
6. White-colored flowers with bright yellow-colored throats.

Plants of the new *Mandevilla* can be compared to plants of the female parent selection. Plants of the new *Mandevilla* differ primarily from plants of the female parent selection in the following characteristics:

1. Plants of the new *Mandevilla* are more upright than and not as vining as plants of the female parent selection.
2. Flowers of plants of the new *Mandevilla* are white in color with bright yellow-colored throats whereas plants of the female parent selection are light pink in color.

Plants of the new *Mandevilla* can be compared to plants of the male parent, 'INMANWHIMP'. Plants of the new *Mandevilla* differ primarily from plants of 'INMANWHIMP' in the following characteristics:

1. Leaves of plants of the *Mandevilla* are broader and darker green than leaves of plants of 'INMANWHIMP'.
2. Flower petals of plants of the new *Mandevilla* are not as pure white in color as flower petals of plants of 'INMANWHIMP'.

Plants of the new *Mandevilla* can also be compared to plants of *Mandevilla sanderi* 'QD2', disclosed in U.S. Plant Pat. No. 32,504. In side-by-side comparisons, plants of the new *Mandevilla* differ primarily from plants of 'QD2' in the following characteristics:

1. Plants of the new *Mandevilla* are more compact than plants of 'QD2'.
2. Leaves of plants of the new *Mandevilla* are smaller than leaves of plants of 'QD2'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Bahwhite' grown in a container.

Figure 2:
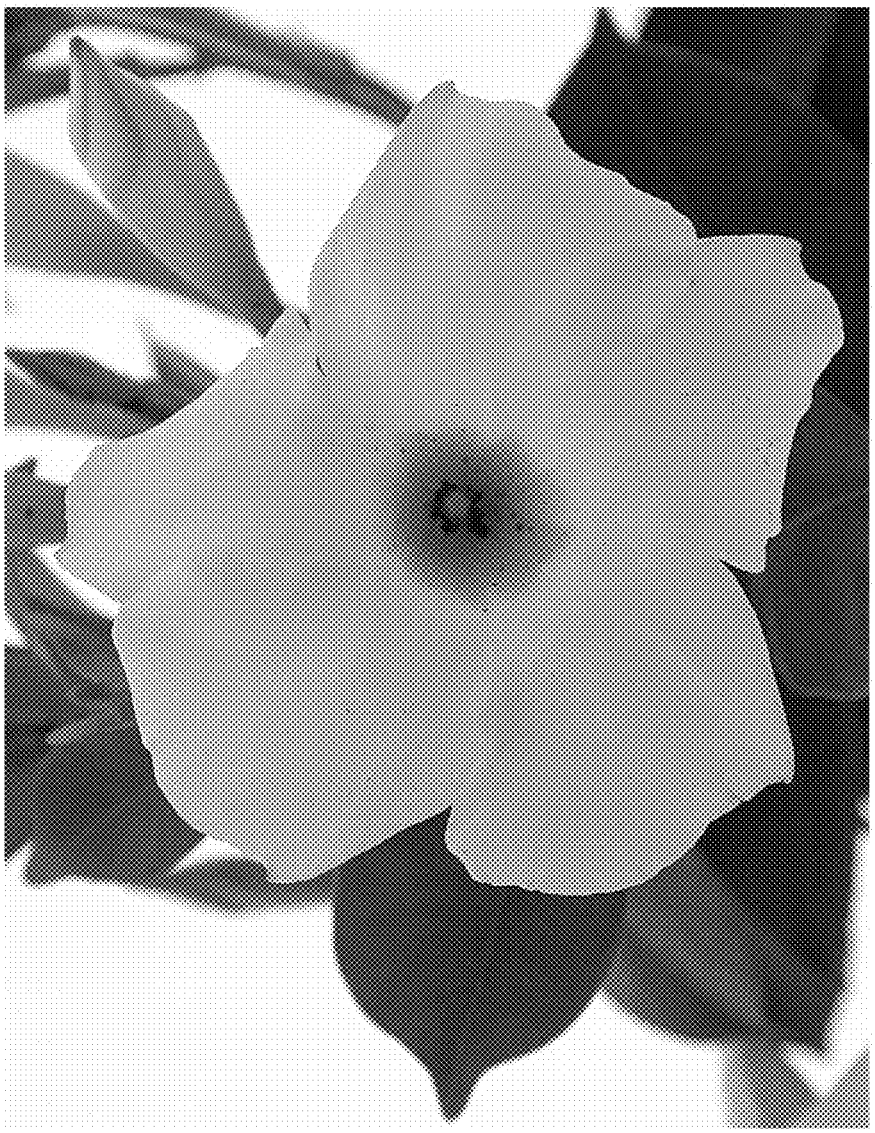

The photograph on the second sheet (FIG. 2) is a close-up view of a typical flower and flower buds of 'Bahwhite'.

DETAILED BOTANICAL DESCRIPTION

The aforementioned photographs and following observations, measurements and values describe plants grown during the spring in 9.5-cm containers with two plants per container in a polyethylene-covered greenhouse in Vicar, Spain and under cultural practices typical of commercial *Mandevilla* production. During the production of the plants, day temperatures ranged from 12 C to 40 C and night temperatures ranged from 8 C to 20 C. Plants were six months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Bahwhite'.

Parentage:

*Female, or seed, parent*.—Proprietary breeding selection of *Mandevilla sanderi* identified as code number 411, not patented.

*Male, or pollen, parent*.—*Mandevilla sanderi* 'INMANWHIMP', disclosed in U.S. Plant Pat. No. 28,276.

Propagation:

*Type*.—By vegetative cuttings.

*Time to initiate roots, summer*.—About 21 days at temperatures ranging from 20 C to 35 C.

*Time to initiate roots, winter*.—About 30 days at temperatures ranging from 20 C to 35 C.

*Time to produce a rooted young plant, summer*.—About 30 to 35 days at temperatures ranging from 20 C to 35 C.

*Time to produce a rooted young plant, winter*.—About 25 to 30 days at temperatures ranging from 15 C to 20 C.

*Root description*.—Thick, fleshy; typically white in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Compact and broadly upright plant habit; broadly oblong to obovate in overall shape; moderately vigorous growth habit and moderate growth rate; freely branching habit.

*Plant height, soil level to top of foliar plane*.—About 20.1 cm.

*Plant height, soil level to top of floral plane*.—About 21.2 cm.

*Plant diameter (spread)*.—About 16.2 cm.

*Lateral branch description*.—Branching habit: Freely branching habit, typically about three lateral branches per plant; pinching enhances lateral branch development. Length: About 11.8 cm. Diameter: About 2.25 mm. Internode length: About 3.1 cm. Aspect: About 20 to 30 degrees from vertical. Strength: Strong. Texture and luster: Smooth, glabrous; slightly glossy; becoming woody with development. Color, developing: Close to 144A. Color, developed: Close to a blend of 144A and 144B; when woody, close to 199A and 199B.

Leaf description:

*Arrangement*.—Opposite, simple.

*Length*.—About 6 cm.

*Width*.—About 3.9 cm.

*Shape*.—Obovate to close to broadly oblong.

*Apex*.—Abruptly acute to short apiculate.

*Base*.—Truncate to rounded.

*Margin*.—Entire, not lobed.

*Texture and luster, upper surface*.—Smooth, glabrous; moderately coriaceous; moderately glossy.

*Texture and luster, lower surface*.—Smooth, glabrous; moderately coriaceous; glossy.

*Venation pattern*.—Pinnate.

*Color*.—Developing leaves, upper surface: Close to 146A. Developing leaves, lower surface: Close to a blend of 152A and N199A. Full expanded leaves, upper surface: Darker than between NN137A and 139A; venation, close to 144A. Fully expanded leaves, lower surface: Close to 146B; venation, close to 145B.

*Petioles*.—Length: About 1.2 cm. Diameter: About 2 mm by 2 mm. Strength: Moderately strong. Texture and luster, upper and lower surfaces: Smooth, glabrous; slightly glossy. Color, upper surface: Close to 144B; margins, close to 144A. Color, lower surface: Close to 144B.

Flower description:

*Flower type and flowering habit*.—Single salverform flowers arranged in terminal and axillary cymes; flowers face outwardly to slightly upright; freely flowering habit with about eight flowers per inflorescence and about 24 flower buds and open flowers developing per plant during the flowering season.

*Natural flowering season*.—Plants flower continuously from spring into the autumn in Spain; plants begin flowering about twelve weeks after propagation (dependent on light level).

*Flower longevity on the plant*.—Individual flowers last about six days; flowers not persistent.

*Fragrance*.—None detected.

*Inflorescence height*.—About 14.2 cm.

*Inflorescence diameter*.—About 11.8 cm.

*Flower buds*.—Length: About 6 cm. Diameter: About 1 cm. Shape: Narrowly oblanceolate. Texture and luster: Smooth, glabrous; slightly glossy. Color: Close to a 145D; towards the apex, slightly tinged with close to 62D; at the base, close to 145A.

*Flowers*.—Appearance: Flared trumpet, corolla fused and five-parted. Diameter: About 7 cm by 7 cm. Depth (length): About 7.2 cm. Throat diameter: About 1.5 cm. Tube length: About 6.3 cm. Tube diameter: Proximally, about 4 mm; distally, about 1.5 cm.

*Corolla*.—Quantity and arrangement: Five petals arranged in a single whorl; lower 67% portion of the petals are fused into a funnelform tube. Petal length, free lobes: About 3.1 cm. Petal width, free lobes: About 3.1 cm. Petal shape and appearance: Unequal broadly spatulate; slightly convex. Petal apex: Short apiculate, unequal. Petal margin: Entire; moderately undulate. Petal texture and luster, upper surface: Smooth, glabrous; moderately velvety; matte to slightly glossy. Petal texture and luster, lower surface: Smooth, glabrous; slightly velvety; slightly glossy. Throat texture: Smooth, glabrous; velvety. Tube texture: Smooth, glabrous; slightly velvety. Color: Petal, when opening, upper surface: Close to 69D and 76D; towards the throat, close to N155B. Petal, when opening, lower surface: Close to N155B and NN155C; towards the margins, close to 69B. Petal, fully opened, upper surface: Close to NN155D; towards the margins, tinged with close to 69C and 69D; venation, close to NN155D; color does not change with subsequent development. Petal, fully opened, lower surface: Close to NN155D; towards the margins, tinged with close to 69D; venation, close to NN155D; color does not change with subsequent development. Throat: At the petal lobe, close to 16C; distally, close to 15A and proximally, close to N144A and N144B; venation, similar to lamina colors. Tube: Distally, close to 159B and proximally, close to 145A; venation, similar to lamina colors.

*Sepals*.—Quantity and arrangement: Five sepals arranged in a single whorl. Length: About 9 mm. Width: About 2.5 mm. Shape: Lanceolate. Apex: Narrowly acuminate. Base: Broadly cuneate and fused. Margin: Entire. Texture and luster, upper surface: Smooth, glabrous; slightly glossy. Texture and luster, lower surface: Smooth, glabrous; matte. Color: When developing, upper surface: Close to 145C; towards the margins and apex, close to 182A. When developing, lower surface: Close to 145A; towards the margins and apex, close to 182A; towards the base, close to 144B. Fully opened, upper surface: Close to 145C; towards the margins and apex, close to 182A. Fully opened, lower surface: Close to 145C; towards the margins and apex, close to 182A and 182B; towards the base, close to 145A.

*Peduncles*.—Length: About 9.9 cm. Diameter: About 2 mm. Strength: Strong. Aspect: About 30 degrees from lateral branch axis. Texture and luster: Smooth, glabrous; moderately glossy. Color: Close to 143C.

*Pedicels*.—Length: About 1.9 cm. Diameter: About 2 mm. Strength: Strong. Aspect: About 30 degrees from peduncle axis. Texture and luster: Smooth, glabrous; moderately glossy. Color: Close to 144B.

*Reproductive organs*.—Stamens: Quantity and arrangement: Typically five; basifixed; anthers connivent. Filament length: About 2 mm. Filament color: Slightly lighter than 151D. Anther shape: Narrowly oblong. Anther size: About 1.25 mm by 9 mm. Anther color: Close to 161D. Pollen amount: None observed. Pistils: Quantity: Typically one. Pistil length: About 3 cm. Style length: About 2.7 cm. Style color: Close to 157D. Stigma diameter: About 2 mm. Stigma shape: Club-shaped, pointed. Stigma color: Close to 146C and 146D. Ovary color: Close to 143C.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5 C to about 40 C and to be suitable for USDA Hardiness Zones 9 to 13.

It is claimed:

1. A new and distinct *Mandevilla* plant named 'Bahwhite' as illustrated and described.

* * * * *